United States Patent [19]

Fujikura et al.

[11] Patent Number: 4,693,845
[45] Date of Patent: Sep. 15, 1987

[54] BORNANA-3-SPIRO-1'-CYCLOPENTANES AND PERFUME COMPOSITIONS COMPRISING THE SAME

[75] Inventors: Yoshiaki Fujikura, Utsunomiya; Akira Yamamuro, Tochigi; Motoki Nakajima, Saitama, all of Japan

[73] Assignee: KAO Corporation, Tokyo, Japan

[21] Appl. No.: 875,682

[22] Filed: Jun. 18, 1986

[30] Foreign Application Priority Data

Jul. 12, 1985 [JP] Japan ................. 60-153641

[51] Int. Cl.$^4$ .......................... A61K 7/46; C11B 9/00; C07C 35/23; C07C 49/417
[52] U.S. Cl. ......................... 512/9; 568/374; 568/375; 568/379; 568/820; 568/821; 568/838; 424/70; 252/174.11
[58] Field of Search .................... 252/522 R; 568/374, 568/375, 379, 807, 838, 821, 816, 820

[56] References Cited

FOREIGN PATENT DOCUMENTS 3346213 7/1984 Fed. Rep. of Germany ...... 568/820
0019738 1/1985 Japan ................. 568/820

Primary Examiner—Werren B. Lone
Attorney, Agent, or Firm—Oblon, Fisher, Spivak, McClelland & Maier

[57] ABSTRACT

Novel bornane-3-spiro-1'-cylopentane derivatives of the following formula (I)

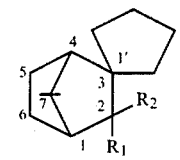

in which $R_1$ and $R_2$ are defined such that when $R_1$ is a hydrogen atom, $R_2$ is a hydroxyl group, or $R_1$ and $R_2$ are joined to form a ketone are obtained from camphor. The derivatives are synthesized in a simple process from an economical starting material, camphor. The derivatives have woody-note and can be widely used in perfumes, soaps, shampoos, hair rinses, cosmetics and the like.

5 Claims, No Drawings

BORNANA-3-SPIRO-1'-CYCLOPENTANES AND PERFUME COMPOSITIONS COMPRISING THE SAME

BACKGROUND OF THE INVENTION (1) Field of the Invention

This invention relates to novel bornane-3-spiro-1'-cyclopentanes and perfume compositions comprising the same.

(2) Description of the Prior Art

At present, perfume materials do not greatly rely on natural matters, but depend chiefly on synthetic perfumes in order to meet various requirements, such as stabilities in supply and quality, low cost and the like.

However, with regard to woody-note to which the present invention is directed, natural perfumes are predominantly used. Taking an increasing demand in future into consideration, the shortage of the natural perfumes is unavoidable. Therefore, it is important to supply synthetic perfumes which emit woody-note.

In general, most compounds having woody-note have complicated polycyclic structures, typical of which are sesqui-terpenes, making it difficult to industrially produce such compounds. Among these polycyclic compounds, tricyclic compounds are particularly difficult to prepare.

SUMMARY OF THE INVENTION

We have made extensive studies on the assumption that if readily available bicyclic monoterpenes are used to prepare tricyclic compounds, the preparation becomes very easy. As a result, we have succeeded in obtaining novel compounds having woody-note from camphor which is stable with respect to cost and supply. The present invention is accomplished on the basis of the above success.

The present invention provides bornane-3-spiro-1'-cyclopentane derivatives of the following formula (I),

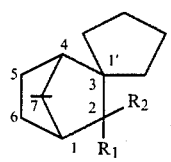

(I)

in which $R_1$ and $R_2$ are defined such that when $R_1$ is a hydrogen atom, $R_2$ is a hydroxyl group, or $R_1$ and $R_2$ are joined to form a ketone, and perfume compositions comprising the same.

DETAILED DESCRIPTION OF THE INVENTION AND PREFERRED EMBODIMENTS

The compounds (I) of the invention are prepared, for example, according to the following reaction scheme:

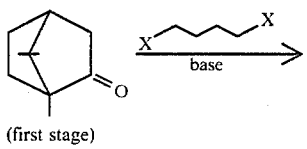

(first stage)

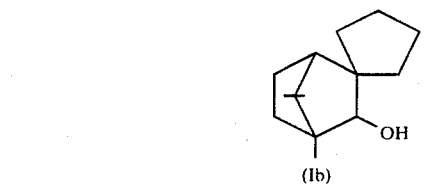

(Ia)
(second stage)

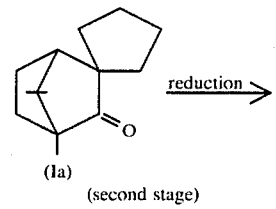

(Ib)

in which X represents a halogen atom.

The reaction of forming a spiro ring in the first stage is effected according to the procedure described, for example, in A. P. Krapcho, Synthesis, 383 (1974). More particularly, camphor and a 1,4-dihalogenobutane are heated and agitated in the presence of a base and a suitable solvent, thereby obtaining compound (Ia).

Examples of the 1,4-dihalogenobutanes include 1,4-dichlorobutane, 1,4-dibromobutane, and 1,4-diiodobutane. Because the chloro product is less reactive and the iodo product is expensive, the dibromo product is preferably used.

The bases may be any bases ordinarily used for alkylation and include, for example, alkali metal amides, alkali metal tertiary alkoxides, alkali metal hydrides and the like. Of these, sodium amide, potassium-t-butoxide and sodium hydrides are preferred.

The solvents used for these purposes include, for example, hydrocarbons such as n-hexane, n-heptane and the like, aromatic hydrocarbons such as benzene, toluene, xylene and the like, ethers such as diethyl ether, tetrahydrofuran (THF), dioxane, dimethyl cellosolve, and the like, and aprotonic, polar solvents such as dimethylformamide (DMF), dimethylsulfoxide (DMSO), hexamethylphosphoamide (HMPA), and the like.

The reduction in the second stage may be effected by any known methods which are used for reduction of ketones. Typical methods include a reduction using a metal hydride such as lithium aluminium hydride or sodium borohydride, and a hydrogenation reaction using a transition metal catalyst such as platinum oxide, ruthenium/carbon, Cu-Cr catalyst or the like.

The reduction using metal hydrides can be effected according to an ordinary procedure described, for example, by L. F. Fieser & M. Fieser, Reagents for Organic Synthesis, John Wiley & Sons Inc., (1967).

On the other hand, the hydrogenation reaction using metal catalysts may be effected in the absence of solvents, but may be carried out in solvents including, for example, saturated hydrocarbons such as n-hexane, alcohols such as methanol, ethanol and the like, or ethers such as diethyl ether, THF, dioxane and the like. The reaction temperature is in the range of from 100° C. to 250° C., preferably from 150° to 250° C.

According to the reduction reaction of the second stage, two isomers of the following formulas (Ibx) and (Ibn):

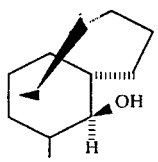

(Ibx)

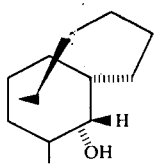

(Ibn)

are produced. The compounds (Ibx) and (Ibn) can be separated, for example, by liquid chromatography.

The thus obtained compounds (Ia), (Ibx) and (Ibn) of the invention have woody-note. When these compounds are formulated in various substrates, useful perfume compositions can be prepared.

The compounds (Ia), (Ibx) and (Ibn) of the invention have all woody-note which are different from one another as follows.

The compound (Ia) has a patchouli-like, slightly earthy woody fragrance with an amber tone similar to sage clary. The compound (Ibx) has a patchouli-like woody amber note with a slight camphor tone. The compound (Ibn) has a vaguely patchouli-like, woody-note.

As described above, the compounds of the invention have inherent odor based on woody-tone and are useful as materials for various perfumes. Accordingly, they can be widely used in various articles requiring flavors or fragrances, such as high quality perfume compositions, perfumes, soaps, shampoos, hair rinses, detergents, cosmetics, sprays, aromatics and the like.

The present invention is more particularly described by way of examples.

EXAMPLE 1

(i) Synthesis of bornane-3-spiro-1'-cyclopentane-2-one:

270 g (1.25 moles) of 1,4-dibromobutane was added, at room temperature, to a solution of a mixture of 152 g (1 mol) of dl-camphor, 100 g of sodium amide (2.56 mols) and 2 liters of n-hexane. Thereafter, the mixture was agitated for 24 hours under reflux condition. After cooling down to room temperature, water was added to the mixture for separation into two phases. The organic phase was neutralized and washed with a dilute hydrochloric acid solution, followed by washing with a saturated sodium thiosulfate solution, then with a saturated sodium carbonate solution, and twice with water. After drying over anhydrous magnesium sulfate, the solvent was distilled off, followed by distillation under reduced pressure to obtain a pure product.

Yield: 146 g (71%)
Boiling Point: 130° C./10mmHg
Elemental analysis: Found C; 81.73%, H; 10.91%. Calculated C; 81.50%, H; 10.75%.
IR(liquid film, cm$^{-1}$) 1740 ($\nu$C=O)
$^1$HNMR (CDCl$_3$ solvent, TMS internal standard, $\nu$)
  2.0-1.3 (complicated multiplet, 13 H)
  1.0 (singlet, —CH$_3$, 3 H)
  0.85 (singlet, —CH$_3$, 6 H)

Mass [m/e, (relative intensity)]206 (M+, 11), 163(40), 109(53), 108(78), 96(70), 95(89), 83(51), 55(52), 41(100)

(ii) Synthesis of bornane-3-spiro-1'-cyclopentane-2-ol:

0.37 g (9.7 mmols) of lithium aluminium hydride was suspended in 5 ml of dry diethyl ether. Into the suspension was dropped a diethyl ether solution (10 ml) of 4 g (19.4 mmols) of bornane-3-spiro-1'-cyclopentane-2-one in about 5 minutes, followed by further reaction for 2 hours under reflux. After completion of the reaction, there were added 0.5 ml of water, 0.5 ml of a 10% aqueous caustic soda solution and 1.5 ml of water in this order. The resulting precipitate was filtered by a glass filter and washed with ether sufficiently. The ether solution was washed twice with a saturated saline solution and dried over anhydrous magnesium sulfate. The organic phase was filtered, followed by removing the solvent by distillation and distillation under reduced pressure to obtain 3.7 g of bornane-3-spiro-1'-cyclopentane-2-ol (yield 92%). A ratio of (Ibx) and (Ibn) was 9:1.

Boiling point: 145° C./14 mmHg [mixture of (Ibx) and (Ibn)]
Elemental analysis [mixture of (Ibx) and (Ibn)]Found C; 80.92%, H; 11.44%. Calculated C; 80.71%, H; 11.61%.

The compounds (Ibx) and (Ibn) can be separated by liquid chromatography. When the separated compounds are recrystallized from n-pentane, pure products can be obtained.

Melting point (sealed tube)
  (Ibx): 32.0° C.
  (Ibn): 64.9° C.
IR (KBr tablet, cm$^{-1}$)
  (Ibx): 3650 (sharp absorption, non-association, $\nu$O—H) 3600-3300 (broad absorption, $\nu$O—H) 1040 ($\nu$C—O)
  (Ibn): 3700-3100 (broad absorption, $\nu$O—H) 1050 ($\nu$C—O)
$^1$HNMR (CDCl$_3$) solvent, TMS internal standard, $\delta$)
  (Ibx): 3.15 (doublet, J =4.2 Hz, >CH13 OH), 2.31 (multiplet, 1 H), 1.75-1.24 (multiplet, 12 H), 1.14-0.95 (singlet and multiplet, 4 H), 0.86 and 0.82 (singlet, CHHD 3$\times$2)
  (Ibn): 3.65 (doublet, 1 H, J=4.7 Hz, >CHOH), 1.85 (multiplet, 2 H), 1.71 1.0 (multiplet, 12 H), 0.97 (singlet, CHHD 3), 0.87 (singlet, CHHD 3), 0.82 (singlet, CHHD 3)
Mass m/e (relative intensity)]
  (Ibx): 208 (M+, 4), 109(20), 108(25), 98(100), 95(60), 81(26), 69(24), 67(25), 55(24), 41(30)
  (Ibn): 208(M+, 5), 108(19), 98(100), 95(58), 84(19), 81(23), 69(22), 67(24), 55(22), 41(27)

EXAMPLE 2

Method using a metal catalyst instead of lithium aluminum hydride in (ii) of Example 1

90 g (0.436 mol) of bornane-3-spiro-1'-cyclopentane-2-one, 100 ml of n-hexane and 4.5 g of 5% ruthenium-/activated carbon catalyst were charged into an autoclave, followed by reaction with hydrogen under 100 atmospheric pressures (gauge) at a temperature of 170 to 190° C. At the time when absorption of hydrogen was stopped, the reaction was determined as completed. The catalyst was filtered, after which the solvent was distilled off, followed by distillation under reduced pressure to obtain a mixture of (Ibx) and (Ibn). The yield was 73.6 g (81%).

EXAMPLE 3

| Perfume for Men's Cologne | |
|---|---|
| Composition: | |
| Oakmoss absolute | 10 (parts by weight) |
| Labdanum resinoid | 5 |
| Galbanum resinoid | 5 |
| Olibanum resinoid | 5 |
| Galaxolide 50[note] | 40 |
| Benzyl salicylate | 50 |
| Heliotropine | 10 |
| Bergamot oil | 150 |
| Lemon oil | 120 |
| Rosemary oil | 80 |
| Jasmine base | 60 |
| Alpha-hexylcinnamic aldehyde | 50 |
| Isobornyl acetate | 15 |
| Lavender oil | 125 |
| Styrallyl acetate | 25 |
| Patchouli oil | 30 |
| Rose base | 20 |
| Eugenol | 15 |
| Geranium oil | 30 |
| Vetiveryl acetate | 20 |
| Cis-3-hexenol | 1 |
| Lime oil | 34 |
| | 900 |

[note]Galaxolide 50 (commercial name of IFF Co., Ltd.): 1,3,4,6,7,8-hexahydro-4,6,6,7,8,8-hexamethylcyclopenta-gamma-2-benzopyran Note) Galaxolide 50 (commercial name of IFF Co., Ltd.): 1,3,4,6,7,8-hexahydro-4,6,6,7,8,8-hexamethylcyclopenta-gamma-benzopyran To 900 parts by weight of the perfume of the above formulation was added 100 parts by weight of bornane-3-spiro-1'-cyclopentane-2-one, thereby obtaining a high-toned perfume imparted with a woody-note and sweetness.

EXAMPLE 4

| Rose-type Perfume | |
|---|---|
| Composition: | |
| Phenyl ethyl alcohol | 200 (parts by weight) |
| Geraniol | 250 |
| Citronellol | 250 |
| Hydroxy citronellal | 50 |
| Citronella oil | 2 |
| Geranium oil | 26 |
| Beta-damaskon | 1 |
| Phenyl acetoaldehyde | 1 |
| Geranyl acetate | 35 |
| Citroneryl acetate | 30 |

EXAMPLE 4-continued

| Rose-type Perfume | |
|---|---|
| Composition: | |
| Alpha-ionone | 5 |
| | 850 |

To 850 parts by weight of the rose base of the above formulation was added 150 parts by weight of bornane-3-spiro-1'-cyclopentane-2-ol (the mixture obtained in (ii) of Example 1) of the invention, to obtain a novel type of rose base which was vigorous and sweet.

What is claim is:

1. A bornane-3-spiro-1'-cyclopentane derivative of formula (I):

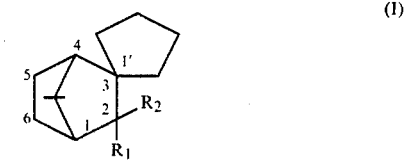

wherein $R_1$ and $R_2$ are such that when $R_1$ is a hydrogen atom, $R_2$ is a hydroxyl group, or $R_1$ and $R_2$ together form a ketone group.

2. The cyclopentane derivative of claim 1, wherein $R_1$ is hydrogen and $R_2$ is hydroxyl.

3. The cyclopentane derivative of claim 1, wherein $R_1$ and $R_2$ together form a ketone group.

4. A perfumed composition, comprising:
a fragence promoting and enhancing amount of a bornane-3-spiro-1'-cyclopentane derivative of formula (I):

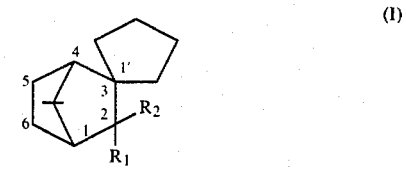

wherein $R_1$ and $R_2$ are such that when $R_1$ is a hydrogen atom, $R_2$ is a hydroxyl group, or $R_1$ and $R_2$ together form a ketone group, in combination with the remaining constitutents of the perfumed composition.

5. The composition of claim 4, wherein said composition is a perfume formulation, a soap, shampoo, hair rinse, detergent, cosmetic, spray or aromatic formulation.

* * * * *